United States Patent [19]
Fischhoff et al.

[11] Patent Number: 5,349,124
[45] Date of Patent: Sep. 20, 1994

[54] INSECT-RESISTANT LETTUCE PLANTS

[75] Inventors: David A. Fischhoff, Webster Groves; Stephen G. Rogers, Chesterfield, both of Mo.

[73] Assignee: Monsanto Company, St. Louis, Mo.

[21] Appl. No.: 836,149

[22] Filed: Feb. 13, 1992

Related U.S. Application Data

[63] Continuation of Ser. No. 185,753, Apr. 25, 1988, abandoned.

[51] Int. Cl.$^5$ .......................... A01H 4/00; C12N 5/14
[52] U.S. Cl. ................. 800/205; 435/240.4; 800/DIG. 13; 424/93.21
[58] Field of Search ............... 800/205, DIG. 13; 435/240.4, 172.3; 424/93 B; 536/23.71

[56] References Cited

U.S. PATENT DOCUMENTS 4,467,036 8/1984 Schnepf et al. .................. 435/320.1

FOREIGN PATENT DOCUMENTS 142924 5/1985 European Pat. Off. .
193259 9/1986 European Pat. Off. .

OTHER PUBLICATIONS

Christon et al. (1986) Plant Physiol. 82:218–221.
Schnepf, et al., "The Amino Acid Sequence of a Crystal Protein from Bacillus thuringiensis Deduced from the DNA Base Sequence" 1985, vol. 260, #10, *J. of Biological Chemistry*, pp. 6264–6272.
Caplan, et al., "Introduction of Genetic Material into Plant Cells" 1983 *Science*, 222:815–821.
Vaeck, et al., "Transgenic Plants Protected from Insect Attack" 1987, *Nature* vol. 328, pp. 33–37.
Barton, et al., "Bacillus thuringiensis Endotoxin Expressed in Transgenic Nicotiana tabacum Provides Resistance to Lepidopteran Insects" 1987, Plant Physiol. 85, pp. 1103–1109.
Fischhoff, et al., "Insect Tolerant Transgenic Tomato Plants" 1987 vol. 5, pp. 807–813, *Biotechnology*.
Adang, et al., "Characterized full length and truncated plasmid clones of the crystal protein of Bacillus thuringiensis subsp. kurstaki HD-73 and their toxicity to Manduca sexta" 1985, *Gene*, 36:289–300.
Schnepf et al. (1985) Journ. Biol. Chem. 260(10):6273–80.
Cole, RA (1987) Ann. Appl. Biol. 111(3):629–640.
Barton et al. (1987) Plant Physiol. 85:1103–09.
Vaeck et al. (1987) Nature 328:33–37.

*Primary Examiner*—Che S. Chereskin
*Attorney, Agent, or Firm*—Dennis R. Hoerner, Jr.; Lawrence M. Lavin, Jr.; Richard H. Shear

[57] ABSTRACT

This present invention describes genetically transformed lettuce cells and transgenic lettuce plants which exhibit toxicity to Lepidopteran larvae.

10 Claims, 16 Drawing Sheets

```
                         -150                      -130
      BamHI    PstI        .                         .
      GGATCCGTCGACCTGCAGGAACACCCTGGGTCAAAAATTGATATTTAGTAA

|- pUC7 ---| PstI |---- B.t. Toxin Gene --------->
                 linker

-110                -90                  -70
             .                  .                    .
      AATTAGTTGCACTTTGTGCATTTTTTCATAAGATGAGTCATATGTTTTAAATTGTAGTAA
           -50                 -30                  -10
             .                  .                    .
      TGAAAAACAGTATTATATCATAATGAATTGGTATCTTAATAAAAGAGATGGAGGTAACTT
             10                  30                   50
              .                   .                    .
      ATGGATAACAATCCGAACATCAATGAATGCATTCCTTATAATTGTTTAAGTAACCCTGAA
      MetAspAsnAsnProAsnIleAsnGluCysIleProTyrAsnCysLeuSerAsnProGlu
             70                  90                  110
              .                   .                    .
      GTAGAAGTATTAGGTGGAGAAAGAATAGAAACTGGTTACACCCCAATCGATATTTCCTTG
      ValGluValLeuGlyGlyGluArgIleGluThrGlyTyrThrProIleAspIleSerLeu
            130                 150                  170
              .                   .                    .
      TCGCTAACGCAATTTCTTTTGAGTGAATTTGTTCCCGGTGCTGGATTTGTGTTAGGACTA
      SerLeuThrGlnPheLeuLeuSerGluPheValProGlyAlaGlyPheValLeuGlyLeu
            190                 210                  230
              .                   .                    .
      GTTGATATAATATGGGGAATTTTTGGTCCCTCTCAATGGGACGCATTTCTTGTACAAATT
      ValAspIleIleTrpGlyIlePheGlyProSerGlnTrpAspAlaPheLeuValGlnIle
            250                 270                  290
              .                   .                    .
      GAACAGTTAATTAACCAAAGAATAGAAGAATTCGCTAGGAACCAAGCCATTTCTAGATTA
      GluGlnLeuIleAsnGlnArgIleGluGluPheAlaArgAsnGlnAlaIleSerArgLeu
            310                 330                  350
              .                   .                    .
      GAAGGACTAAGCAATCTTTATCAAATTTACGCAGAATCTTTTAGAGAGTGGGAAGCAGAT
      GluGlyLeuSerAsnLeuTyrGlnIleTyrAlaGluSerPheArgGluTrpGluAlaAsp
            370                 390                  410
              .                   .                    .
      CCTACTAATCCAGCATTAAGAGAAGAGATGCGTATTCAATTCAATGACATGAACAGTGCC
      ProThrAsnProAlaLeuArgGluGluMetArgIleGlnPheAsnAspMetAsnSerAla
            430                 450                  470
```

FIG. 1a

```
CTTACAACCGCTATTCCTCTTTTTGCAGTTCAAAATTATCAAGTTCCTCTTTTATCAGTA
LeuThrThrAlaIleProLeuPheAlaValGlnAsnTyrGlnValProLeuLeuSerVal
      490             510             530

TATGTTCAAGCTGCAAATTTACATTTATCAGTTTTGAGAGATGTTTCAGTGTTTGGACAA
TyrValGlnAlaAlaAsnLeuHisLeuSerValLeuArgAspValSerValPheGlyGln
      550             570             590

AGGTGGGGATTTGATGCCGCGACTATCAATAGTCGTTATAATGATTTAACTAGGCTTATT
ArgTrpGlyPheAspAlaAlaThrIleAsnSerArgTyrAsnAspLeuThrArgLeuIle
      610             630             650

GGCAACTATACAGATCATGCTGTACGCTGGTACAATACGGGATTAGAGCGTGTATGGGGA
GlyAsnTyrThrAspHisAlaValArgTrpTyrAsnThrGlyLeuGluArgValTrpGly
      670             690             710

CCGGATTCTAGAGATTGGATAAGATATAATCAATTTAGAAGAGAATTAACACTAACTGTA
ProAspSerArgAspTrpIleArgTyrAsnGlnPheArgArgGluLeuThrLeuThrVal
      730             750             770

TTAGATATCGTTTCTCTATTTCCGAACTATGATAGTAGAACGTATCCAATTCGAACAGTT
LeuAspIleValSerLeuPheProAsnTyrAspSerArgThrTyrProIleArgThrVal
      790             810             830

TCCCAATTAACAAGAGAAATTTATACAAACCCAGTATTAGAAAATTTTGATGGTAGTTTT
SerGlnLeuThrArgGluIleTyrThrAsnProValLeuGluAsnPheAspGlySerPhe
      850             870             890

CGAGGCTCGGCTCAGGGCATAGAAGGAAGTATTAGGAGTCCACATTTGATGGATATACTT
ArgGlySerAlaGlnGlyIleGluGlySerIleArgSerProHisLeuMetAspIleLeu
      910             930             950

AATAGTATAACCATCTATACGGATGCTCATAGAGGAGAATATTATTGGTCAGGGCATCAA
AsnSerIleThrIleTyrThrAspAlaHisArgGlyGluTyrTyrTrpSerGlyHisGln
      970             990            1010

ATAATGGCTTCTCCTGTAGGGTTTTCGGGGCCAGAATTCACTTTTCCGCTATATGGAACT
IleMetAlaSerProValGlyPheSerGlyProGluPheThrPheProLeuTyrGlyThr
     1030            1050            1070

ATGGGAAATGCAGCTCCACAACAACGTATTGTTGCTCAACTAGGTCAGGGCGTGTATAGA
MetGlyAsnAlaAlaProGlnGlnArgIleValAlaGlnLeuGlyGlnGlyValTyrArg
     1090            1110            1130
```

FIG. 1b

```
ACATTATCGTCCACCTTATATAGAAGACCTTTTAATATAGGGATAAATAATCAACAACTA
ThrLeuSerSerThrLeuTyrArgArgProPheAsnIleGlyIleAsnAsnGlnGlnLeu
      1150                1170                1190

TCTGTTCTTGACGGGACAGAATTTGCTTATGGAACCTCCTCAAATTTGCCATCCGCTGTA
SerValLeuAspGlyThrGluPheAlaTyrGlyThrSerSerAsnLeuProSerAlaVal
      1210                1230                1250

TACAGAAAAAGCGGAACGGTAGATTCGCTGGATGAAATACCGCCACAGAATAACAACGTG
TyrArgLysSerGlyThrValAspSerLeuAspGluIleProProGlnAsnAsnAsnVal
      1270                1290                1310

CCACCTAGGCAAGGATTTAGTCATCGATTAAGCCATGTTTCAATGTTTCGTTCAGGCTTT
ProProArgGlnGlyPheSerHisArgLeuSerHisValSerMetPheArgSerGlyPhe
      1330                1350                1370

AGTAATAGTAGTGTAAGTATAATAAGAGCTCCTATGTTCTCTTGGATACATCGTAGTGCT
SerAsnSerSerValSerIleIleArgAlaProMetPheSerTrpIleHisArgSerAla
      1390                1410                1430

GAATTTAATAATATAATTCCTTCATCACAAATTACACAAATACCTTTAACAAAATCTACT
GluPheAsnAsnIleIleProSerSerGlnIleThrGlnIleProLeuThrLysSerThr
      1450                1470                1490

AATCTTGGCTCTGGAACTTCTGTCGTTAAAGGACCAGGATTTACAGGAGGAGATATTCTT
AsnLeuGlySerGlyThrSerValValLysGlyProGlyPheThrGlyGlyAspIleLeu
      1510                1530                1550

CGAAGAACTTCACCTGGCCAGATTTCAACCTTAAGAGTAAATATTACTGCACCATTATCA
ArgArgThrSerProGlyGlnIleSerThrLeuArgValAsnIleThrAlaProLeuSer
      1570                1590                1610

CAAAGATATCGGGTAAGAATTCGCTACGCTTCTACCACAAATTTACAATTCCATACATCA
GlnArgTyrArgValArgIleArgTyrAlaSerThrThrAsnLeuGlnPheHisThrSer
      1630                1650                1670

ATTGACGGAAGACCTATTAATCAGGGGAATTTTTTCAGCAACTATGAGTAGTGGGAGTAAT
IleAspGlyArgProIleAsnGlnGlyAsnPheSerAlaThrMetSerSerGlySerAsn
      1690                1710                1730
       . HindIII .
TTACAGTCCGGAAGCTTTAGGACTGTAGGTTTTACTACTCCGTTTAACTTTTCAAATGGA
LeuGlnSerGlySerPheArgThrValGlyPheThrThrProPheAsnPheSerAsnGly
      1750                1770                1790
```

FIG. 1c

```
TCAAGTGTATTTACGTTAAGTGCTCATGTCTTCAATTCAGGCAATGAAGTTTATATAGAT
SerSerValPheThrLeuSerAlaHisValPheAsnSerGlyAsnGluValTyrIleAsp
    1810              1830              1850

CGAATTGAATTTGTTCCGGCAGAAGTAACCTTTGAGGCAGAATATGATTTAGAAAGAGCA
ArgIleGluPheValProAlaGluValThrPheGluAlaGluTyrAspLeuGluArgAla
    1870              1890              1910

CAAAAGGCGGTGAATGAGCTGTTTACTTCTTCCAATCAAATCGGGTTAAAAACAGATGTG
GlnLysAlaValAsnGluLeuPheThrSerSerAsnGlnIleGlyLeuLysThrAspVal
    1930              1950              1970

ACGGATTATCATATTGATCAAGTATCCAATTTAGTTGAGTGTTTATCTGATGAATTTTGT
ThrAspTyrHisIleAspGlnValSerAsnLeuValGluCysLeuSerAspGluPheCys
    1990              2010              2030

CTGGATGAAAAAAAGAATTGTCCGAGAAAGTCAAACATGCGAAGCGACTTAGTGATGAG
LeuAspGluLysLysGluLeuSerGluLysValLysHisAlaLysArgLeuSerAspGlu
    2050              2070              2090

CGGAATTTACTTCAAGATCCAAACTTTAGAGGGATCAATAGACAACTAGACCGTGGCTGG
ArgAsnLeuLeuGlnAspProAsnPheArgGlyIleAsnArgGlnLeuAspArgGlyTrp
    2110              2130              2150

AGAGGAAGTACGGATATTACCATCCAAGGAGGCGATGACGTATTCAAAGAGAATTACGTT
ArgGlySerThrAspIleThrIleGlnGlyGlyAspAspValPheLysGluAsnTyrVal
    2170              2190              2210
           .KpnI
ACGCTATTGGGTACCTTTGATGAGTGCTATCCAACGTATTTATATCAAAAAATAGATGAG
ThrLeuLeuGlyThrPheAspGluCysTyrProThrTyrLeuTyrGlnLysIleAspGlu
    2230              2250              2270

TCGAAATTAAAAGCCTATACCCGTTACCAATTAAGAGGGTATATCGAAGATAGTCAAGAC
SerLysLeuLysAlaTyrThrArgTyrGlnLeuArgGlyTyrIleGluAspSerGlnAsp
    2290              2310              2330

TTAGAAATCTATTTAATTCGCTACAATGCCAAACACGAAACAGTAAATGTGCCAGGTACG
LeuGluIleTyrLeuIleArgTyrAsnAlaLysHisGluThrValAsnValProGlyThr
    2350              2370              2390

GGTTCCTTATGGCCGCTTTCAGCCCCAAGTCCAATCGGAAAATGTGCCCATCATTCCCAT
GlySerLeuTrpProLeuSerAlaProSerProIleGlyLysCysAlaHisHisSerHis
    2410              2430              2450
```

FIG. 1d

```
CATTTCTCCTTGGACATTGATGTTGGATGTACAGACTTAAATGAGGACTTAGGTGTATGG
HisPheSerLeuAspIleAspValGlyCysThrAspLeuAsnGluAspLeuGlyValTrp
    2470              2490              2510

GTGATATTCAAGATTAAGACGCAAGATGGCCATGAAAGACTAGGAAATCTAGAATTTCTC
ValIlePheLysIleLysThrGlnAspGlyHisGluArgLeuGlyAsnLeuGluPheLeu
    2530              2550              2570

GAAGGAAGAGCACCATTAGTAGGAGAAGCACTAGCTCGTGTGAAAAGAGCGGAGAAAAAA
GluGlyArgAlaProLeuValGlyGluAlaLeuAlaArgValLysArgAlaGluLysLys
    2590              2610              2630

TGGAGAGACAAACGTGAAAAATTGGAATGGGAAACAAATATTGTTTATAAAGAGGCAAAA
TrpArgAspLysArgGluLysLeuGluTrpGluThrAsnIleValTyrLysGluAlaLys
    2650              2670              2690

GAATCTGTAGATGCTTTATTTGTAAACTCTCAATATGATAGATTACAAGCGGATACCAAC
GluSerValAspAlaLeuPheValAsnSerGlnTyrAspArgLeuGlnAlaAspThrAsn
    2710              2730              2750
 NruI                                    HindIII
ATCGCGATGATTCATGCGGCAGATAAACGCGTTCATAGCATTCGAGAAGCTTATCTGCCT
IleAlaMetIleHisAlaAlaAspLysArgValHisSerIleArgGluAlaTyrLeuPro
    2770              2790              2810

GAGCTGTCTGTGATTCCGGGTGTCAATGCGGCTATTTTTGAAGAATTAGAAGGGCGTATT
GluLeuSerValIleProGlyValAsnAlaAlaIlePheGluGluLeuGluGlyArgIle
    2830              2850              2870

TTCACTGCATTCTCCCTATATGATGCGAGAAATGTCATTAAAAATGGTGATTTTAATAAT
PheThrAlaPheSerLeuTyrAspAlaArgAsnValIleLysAsnGlyAspPheAsnAsn
    2890              2910              2930

GGCTTATCCTGCTGGAACGTGAAAGGGCATGTAGATGTAGAAGAACAAAACAACCACCGT
GlyLeuSerCysTrpAsnValLysGlyHisValAspValGluGluGlnAsnAsnHisArg
    2950              2970              2990

TCGGTCCTTGTTGTTCCGGAATGGGAAGCAGAAGTGTCACAAGAAGTTCGTGTCTGTCCG
SerValLeuValValProGluTrpGluAlaGluValSerGlnGluValArgValCysPro
    3010              3030              3050

GGTCGTGGCTATATCCTTCGTGTCACAGCGTACAAGGAGGGATATGGAGAAGGTTGCGTA
GlyArgGlyTyrIleLeuArgValThrAlaTyrLysGluGlyTyrGlyGluGlyCysVal
    3070              3090              3110
```

FIG. 1e

```
ACCATTCATGAGATCGAGAACAATACAGACGAACTGAAGTTTAGCAACTGTGTAGAAGAG
ThrIleHisGluIleGluAsnAsnThrAspGluLeuLysPheSerAsnCysValGluGlu
      3130              3150              3170

GAAGTATATCCAAACAACACGGTAACGTGTAATGATTATACTGCGACTCAAGAAGAATAT
GluValTyrProAsnAsnThrValThrCysAsnAspTyrThrAlaThrGlnGluGluTyr
      3190              3210              3230

GAGGGTACGTACACTTCTCGTAATCGAGGATATGACGGAGCCTATGAAAGCAATTCTTCT
GluGlyThrTyrThrSerArgAsnArgGlyTyrAspGlyAlaTyrGluSerAsnSerSer
      3250              3270              3290

GTACCAGCTGATTATGCATCAGCCTATGAAGAAAAAGCATATACAGATGGACGAAGAGAC
ValProAlaAspTyrAlaSerAlaTyrGluGluLysAlaTyrThrAspGlyArgArgAsp
      3310              3330              3350

AATCCTTGTGAATCTAACAGAGGATATGGGGATTACACACCACTACCAGCTGGCTATGTG
AsnProCysGluSerAsnArgGlyTyrGlyAspTyrThrProLeuProAlaGlyTyrVal
      3370              3390              3410
            ScaI
ACAAAAGAATTAGAGTACTTCCCAGAAACCGATAAGGTATGGATTGAGATCGGAGAAACG
ThrLysGluLeuGluTyrPheProGluThrAspLysValTrpIleGluIleGlyGluThr
      3430              3450              3470

GAAGGAACATTCATCGTGGACAGCGTGGAATTACTTCTTATGGAGGAATAATATATGCTT
GluGlyThrPheIleValAspSerValGluLeuLeuLeuMetGluGluEnd
      3490              3510              3530

TAAAATGTAAGGTGTGCAAATAAAGAATGATTACTGACTTGTATTGACAGATAAATAAGG
      3550              3570              3590

AAATTTTTATATGAATAAAAAACGGGCATCACTCTTAAAAGAATGATGTCCGTTTTTTGT
      3610              3630              3650
                                                        KpnI
ATGATTTAACGAGTGATATTTAAATGTTTTTTTGCGAAGGCTTTACTTAACGGGGTACC
```

FIG. 1f

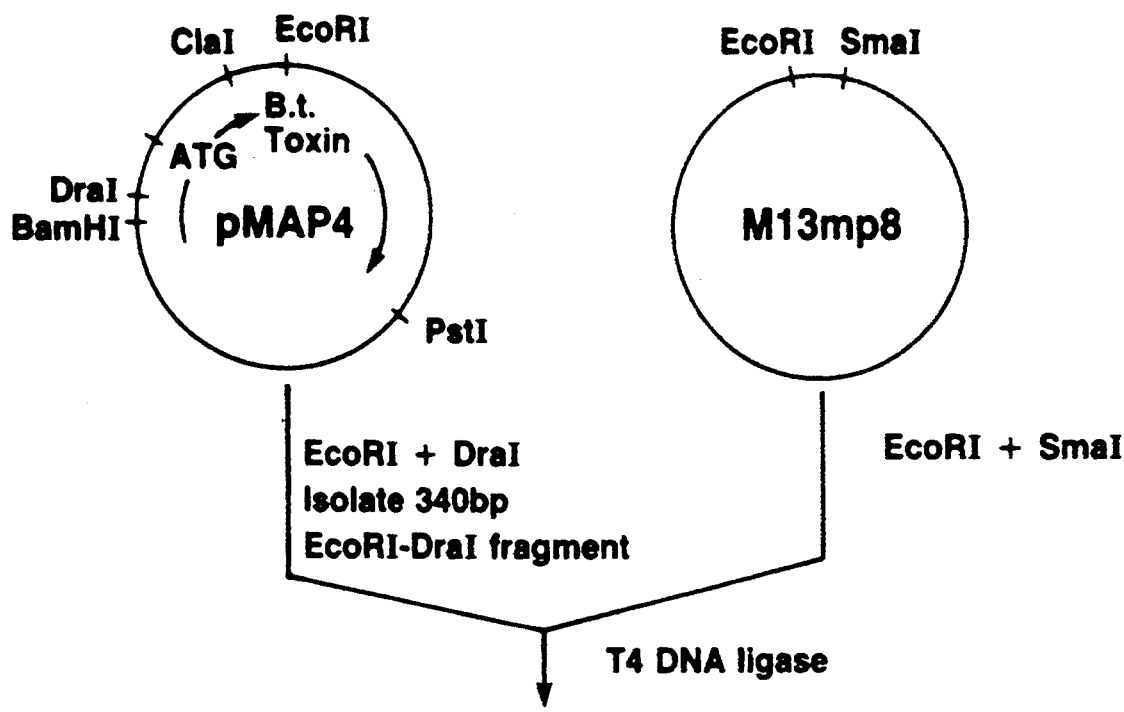
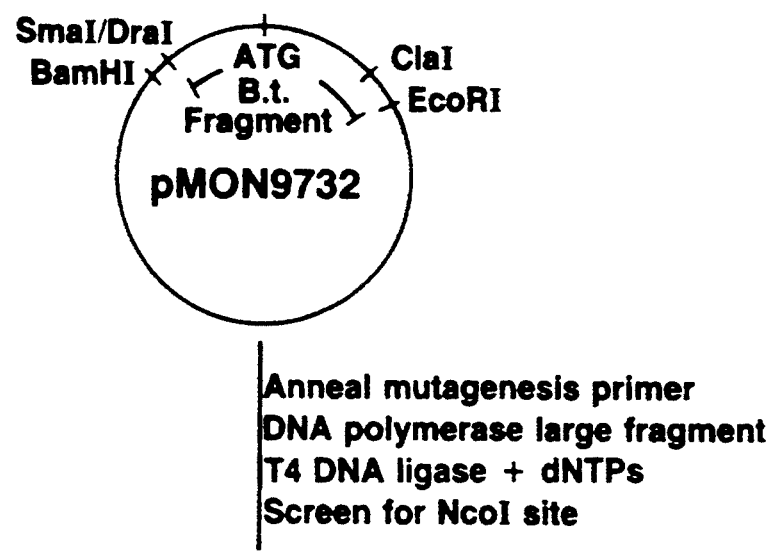
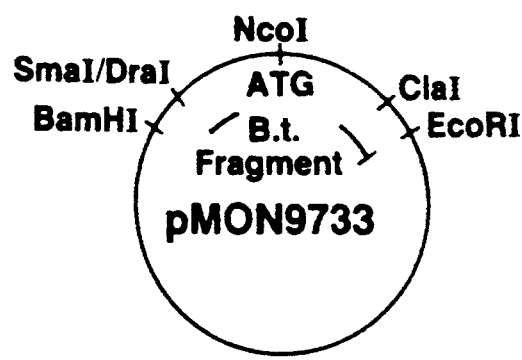
FIG 2

INSECT-RESISTANT LETTUCE PLANTS

This is a file wrapper continuation of application Ser. No. 07/185,753, filed Apr. 25, 1988 now abandoned.

This invention relates to transgenic plants exhibiting toxicity toward insects, and, more particularly, to lettuce (genus Lactuca) plants containing a chimeric gene encoding and expressing a *Bacillus thuringiensis* (*B.t.*) toxin protein.

BACKGROUND OF THE INVENTION

The desirability to transform plant cells by insertion of a plant expressable gene encoded for the toxin protein of Lepidopteran-type *Bacillus thuringiensis* (*B.t.*) and to regenerate transgenic plants exhibiting insect resistance from such cells is known. European patent applications 84306494.0 and 86300291.1, publication numbers 142,924 and 193,259, respectively. Transgenic tobacco plants expressing genes for insecticidal *B.t.* proteins have been made. However, only plants containing truncated *B.t.* genes were insecticidal and plants containing the full-length *B.t.* gene had no greater toxicity toward insects than control plants containing only a selectable marker. M. Vaeck, et al., *Nature*, Vol. 328, July 1987, 33–37, and K. A. Barton, et al., Plant Physiol., (1987) 85, 1103–1109. Transgenic tomato plants expressing genes for insecticidal *B.t.* proteins have also been made. Plants containing both truncated and full-length genes were produced but recovery of transgenic plants was significantly greater when truncated *B.t.* genes were employed than when the full-length *B.t.* gene was used. Significantly, the plants containing the truncated *B.t.* gene exhibited greater insect mortality than the plants containing the full-length *B.t.* gene; D. A. Fischhoff, et al., *Bio/Technology*, Vol. 5, (1987) 807–813.

Studies have shown that the Lepidopteran-type full-length toxin protein produced in bacteria is 13 times more toxic than 80%–50% shortened versions of the toxin protein; M. J. Adang, et al., *Gene* 36 (1986) 289–300. Thus, expression of the full-length gene product in plants may produce a more potent toxin protein and which protein may be efficacious against a broader spectrum of Lepidopteran insects.

SUMMARY OF THE INVENTION

It has now been discovered that lettuce plants exhibiting toxicity toward Lepidopteran insects can be produced by regeneration from differentiated transformed lettuce plant cells containing a chimeric gene having a DNA coding sequence which encodes essentially for the full-length toxin protein of *Bacillus thuringiensis* and which gene expresses a protein toxic toward Lepidopteran larvae. Transformed lettuce plant cells of the invention are produced by conventional transformation techniques by insertion of a chimeric gene having a DNA coding sequence encoding for the full-length *B.t.* toxin protein. The transformed cells are cultured and regenerated via conventional techniques into lettuce plants exhibiting Lepidopteran insect toxicity which trait is sexually reproducible and exhibited in progeny. Unlike transgenic tomato plants, the transgenic lettuce plants of this invention exhibit Lepidopteran insect toxicity equal or greater than the toxicity of transgenic lettuce plants containing a truncated *B.t.* gene.

BRIEF DESCRIPTION OF THE DRAWINGS

FIGS. 1a–1f illustrates the coding sequence for a crystal protein toxin of *Bacillus thuringiensis* subspecies *kurstaki* HD-1.

FIG. 2 illustrates the preparation of plasmid pMON9733.

DESCRIPTION OF THE PREFERRED EMBODIMENTS

Figure 3:
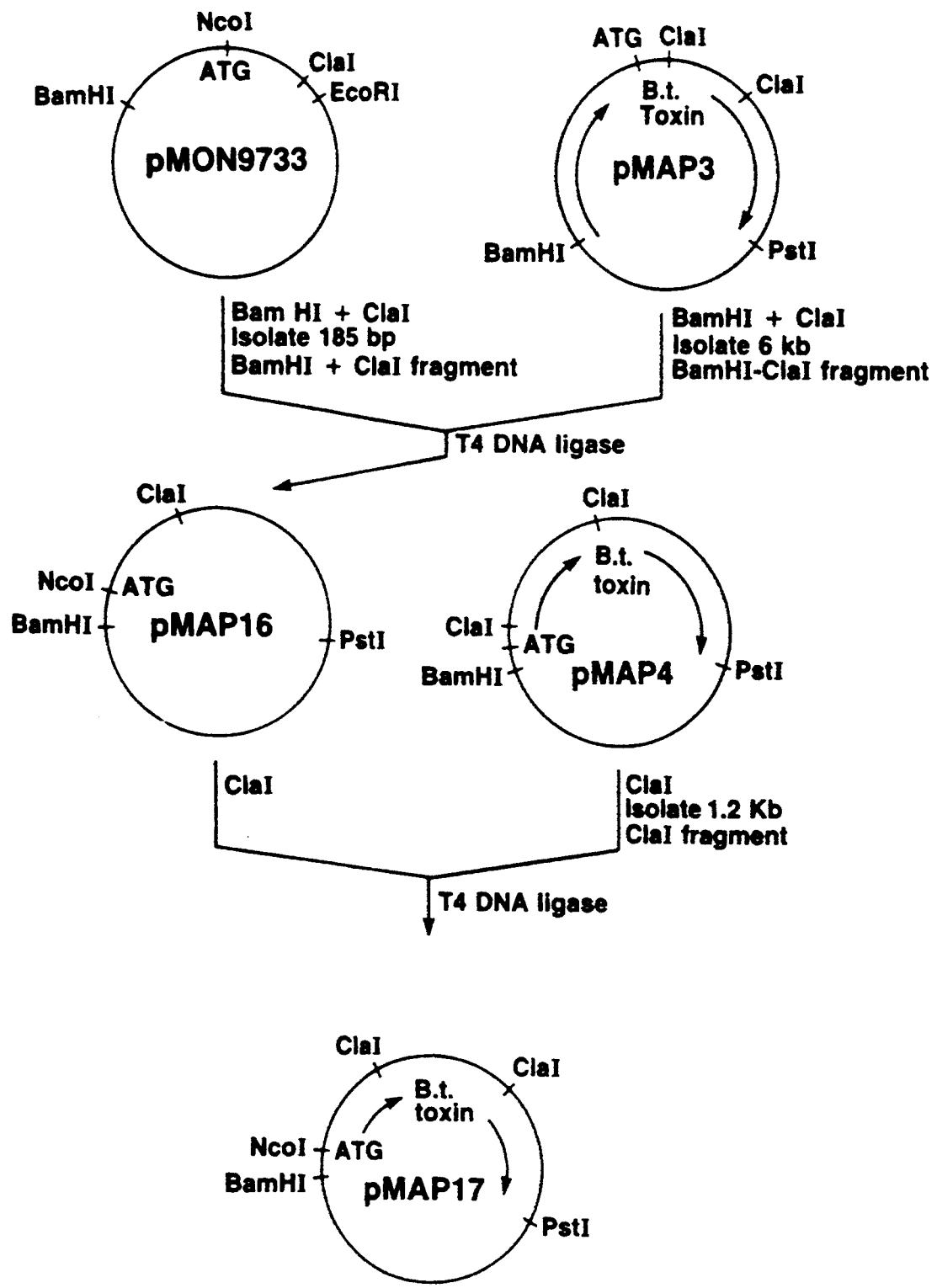
FIG. 3 illustrates the preparation of plasmid pMAP17.

Coding sequences for Lepidopteran-type full-length toxin protein are known, for example, see Vaeck, et al., Barton, et al., Fischhoff, et al. supra. The DNA sequences encoding the full-length toxin protein can be chemically synthesized or can be isolated from genomic libraries and constructed therefrom by conventional techniques. Examples of *Bacillus thuringiensis* species suitable as sources for such DNA coding sequence are *kurstaki* subspecies HD-1 and HD-73, *berliner, sotto, thuringiensis, tolworthi, dendrolimus, alesti, galleriae, aizawai* and *subtoxicus*.

Any plant gene which expresses in plants may be used in the practice of this invention. The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which causes addition of polyadenylate nucleotides to the 3' end of the RNA.

Transcription of DNA into mRNA is regulated by a region of DNA usually referred to as the "promoter". The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose bis-phosphate carboxylase (ssRUBISCO, a very abundant plant polypeptide), and promoters of genes encoding hydroxproline-rich glycoproteins. All of these promoters have been used to create various types of DNA constructs which have been expressed in plants; see e.g., PCT publication WO 84/02913 (Rogers, et al., Monsanto).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO nopaline synthase (NOS) and mannopine synthase (MAS) genes. As described below, it is preferred that the particular promoter selected should be capable of causing sufficient expression to result in the production of toxin protein. The amount of toxin protein needed to induce resistance may vary with the species of insect to be protected against. Accordingly, while the CaMV35S promoter is preferred, it should be understood that this promoter may not be the optimal one for all embodiments of the present invention.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g. promoters derived by means of ligation with operator regions, random or controlled mutagenesis, etc.

A coding sequence used in a DNA construct of this invention may be modified, if desired, to create mutants, either by random or controlled mutagenesis, using methods known to those skilled in the art. Such mutants and variants are therefore within the scope of the present invention.

The 3' non-translated region contains a polyadenylation signal which functions in plants to cause the addition of polyadenylate nucleotides to the 3' end of the mRNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the RuBP carboxylase gene. An example of a preferred 3' region is that from the NOS gene, described in greater detail in the examples below.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA'S, from suitable eukaryotic genes or from a synthetic gene sequence.

The genes employed in the practice of the present invention can be inserted into the genome of a plant by any suitable method. Suitable plant transformation vectors include those derived from a tumor-inducing plasmid of Agrobacterium such as those described by Herrera-Estralla, et al. (*Nature* 303:209, 1983), Bevan, et al. (*Nature* 304:184, 1983), Klee, et al. (*Bio/Technology* 3:637, 1985), Fraley, et al. (*Bio/Technology* 3:629, 1985), and Schilperoort, et al. (EPO publication 120,516). In addition to plant transformation vectors derived from tumor-inducing plasmids of Agrobacterium, alternative methods can be used to insert genes into plant cells. Such methods may involve, for example, the use of liposomes, electroporation, gene gun and chemicals that increase the free DNA uptake. Plant cells transformed with the *B.t.* gene are regenerated into whole (differentiated) plants which exhibit enhanced insect resistance.

Choice of methodology for the regeneration step is not critical. A preferred regeneration protocol is described in detail by Michelmore, et al. *Plant Cell Reports* (1987) 439–442, which is incorporated herein by reference.

EXAMPLE 1

DESCRIPTION OF PREFERRED EMBODIMENTS

The insecticidal toxin gene from *Bacillus thuringiensis* subspecies *kurstaki* HD-1 has been previously described by Watrud, et al. (1985) *Engineered Organisms in the Environment-Scientific Issues* ASM Press, Washington, D.C. The toxin gene is contained on a 4.6 kb fragment of *B.t.* DNA in plasmid pMAP4. The DNA sequence of 3734 nucleotides of pMAP4, including the entire toxin protein coding sequence, is determined by the chain termination method of Sanger, et al. (1977) *P.N.A.S., USA* 74, 5463–5467. The DNA sequence and the derived amino acid sequence for the toxin protein are shown in FIG. 1. Nucleotide coordinates referred to hereinafter are based on the numbering of FIG. 1.

This sequence includes 171 nucleotides upstream of the translational initiation codon and extends through a KpnI site 188 nucleotides after the translational termination codon. The first nucleotide of the protein coding sequence is labeled position +1. DNA sequences from nucleotide −75 to nucleotide 220 and from nucleotide 3245 to 3650 are also determined by the chemical method of Maxam and Gilbert (1977) *P.N.A.S., USA* 74, 560–564. The DNA sequence from −171 to −160 is from the known sequence of the plasmid vector pUC7 (Vieira, 1982). DNA sequence from −159 to −153 is from a chemically synthesized PstI linker (New England Biolabs); the three nucleotides from −152 to −150 are derived from the known cleavage site for restriction enzyme HpaI. The sequence from nucleotide −149 to −76 is inferred from known 5'-flanking sequences of other *B.t.* toxin genes.

EXAMPLE 2

CHIMERIC *B.t.* TOXIN GENES FOR PLANT TRANSFORMATION WITH CaMV35S PROMOTER

A. Full-Length Toxin

To make a chimeric gene encoding the toxin protein of *B.t.* a NcoI site is introduced at the translational initiation codon (ATG) of the DNA encoding the *B.t.* toxin such that the ATG codon is contained within the NcoI recognition site (CCATGG). DNA sequence analysis of the region of the toxin gene around the initiator codon revealed the sequence:

```
5'-GAGATGGAGGTAACTTATGGATAACAATCCGA-3'
              Met Asp Asn Asn Pro
```

To introduce the desired NcoI site, the sequence around the ATG from TTATGG is changed to CCATGG. Referring to FIG. 2, a 340 bp DraI-EcoRI fragment which includes the translational initiation region is subcloned from pMAP4 between the SmaI and EcoRI sites of the filamentous bacteriophage vector M13mp8. This plasmid is named pMON9732. Single-stranded phage DNA from this construct contains the noncoding strand of the toxin gene sequence.

Site-specific mutagenesis is performed on single-stranded DNA from this construct by the method of Zoller and Smith (1983) utilizing as a primer a synthetic oligonucleotide of the sequence:

5'-GAGATGGAGGTAACCCATGGATAACAATCC-3'

Following mutagenesis a clone containing the desired change is identified by digestion with NcoI, and the presence of the NcoI site is confirmed by DNA sequence analysis. This clone is designated pMON9733.

An intact toxin gene is constructed which incorporated the NcoI site from the site-specific mutagenesis described above. Referring to FIG. 3, pMAP3 is digested with BamHI and ClaI and a fragment containing pUC8 vector and the toxin gene from the ClaI site at position 1283 to the PstI site beyond the end of the gene is isolated. A 185 bp fragment extending from the BamHI site in the mp8 multilinker to the ClaI site at position 106 is isolated from pMON9733. These two fragments are ligated to create pMAP16. pMAP16 contains the NcoI site at the ATG but is missing the segment of the toxin gene between the ClaI sites at 106 and 1283. The ClaI fragment is isolated from pMAP4 and ligated with ClaI digested pMAP16. A plasmid containing this inserted ClaI fragment in the proper orientation to reconstruct a functional toxin gene is identified and designated pMAP17. *E. coli* containing this plasmid produced a protein of about 134,000 daltons which reacts with antibodies prepared against purified crystal toxin protein from *Bacillus thuringiensis* subspecies *kurstaki* HD-1 at levels comparable to those produced by *E. coli* containing pMAP4. *E. coli* containing pMAP17 is toxic to the Lepidopteran larvae *Manduca sexta*.

Figure 4:
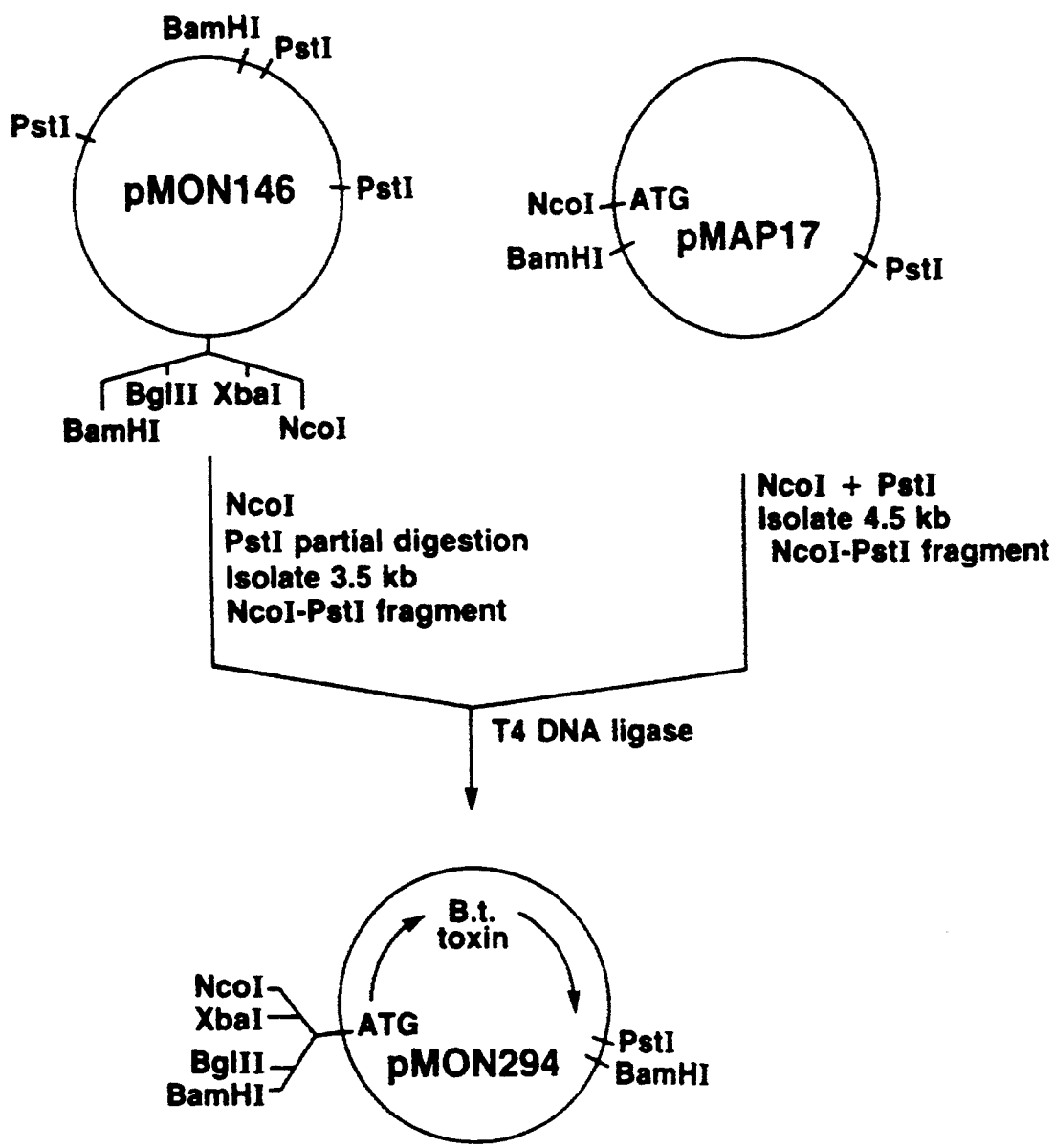
FIG. 4 illustrates the preparation of plasmid pMON294.

To facilitate construction of chimeric toxin genes in plant transformation vectors, BamHI and BglII sites are introduced just upstream of the NcoI site in the toxin gene. Referring to FIG. 4, plasmid pMAP146 is used as a source of a synthetic linker containing restriction sites for BamHI, BglII, XbaI and NcoI as shown:

5'-GGATCCAGATCTGTTGTAAGGAGTCTAGACCATGGATC-3'
    BamHI  BglII              XbaI   NcoI pMON146 is partially digested with PstI and then is digested to completion with NcoI, and a 3.5 kb NcoI-PstI fragment is isolated. The 4.5 kb NcoI-PstI fragment containing the entire toxin gene is isolated from pMAP17, and this fragment is ligated with the 3.5 kb pMON146 fragment. A plasmid containing these two fragments is designated pMON294. In pMON294 a BamHI and a BglII site are just upstream of the initiation codon for the toxin protein, and a BamHI site is just downstream of the PstI site.

Figure 5:
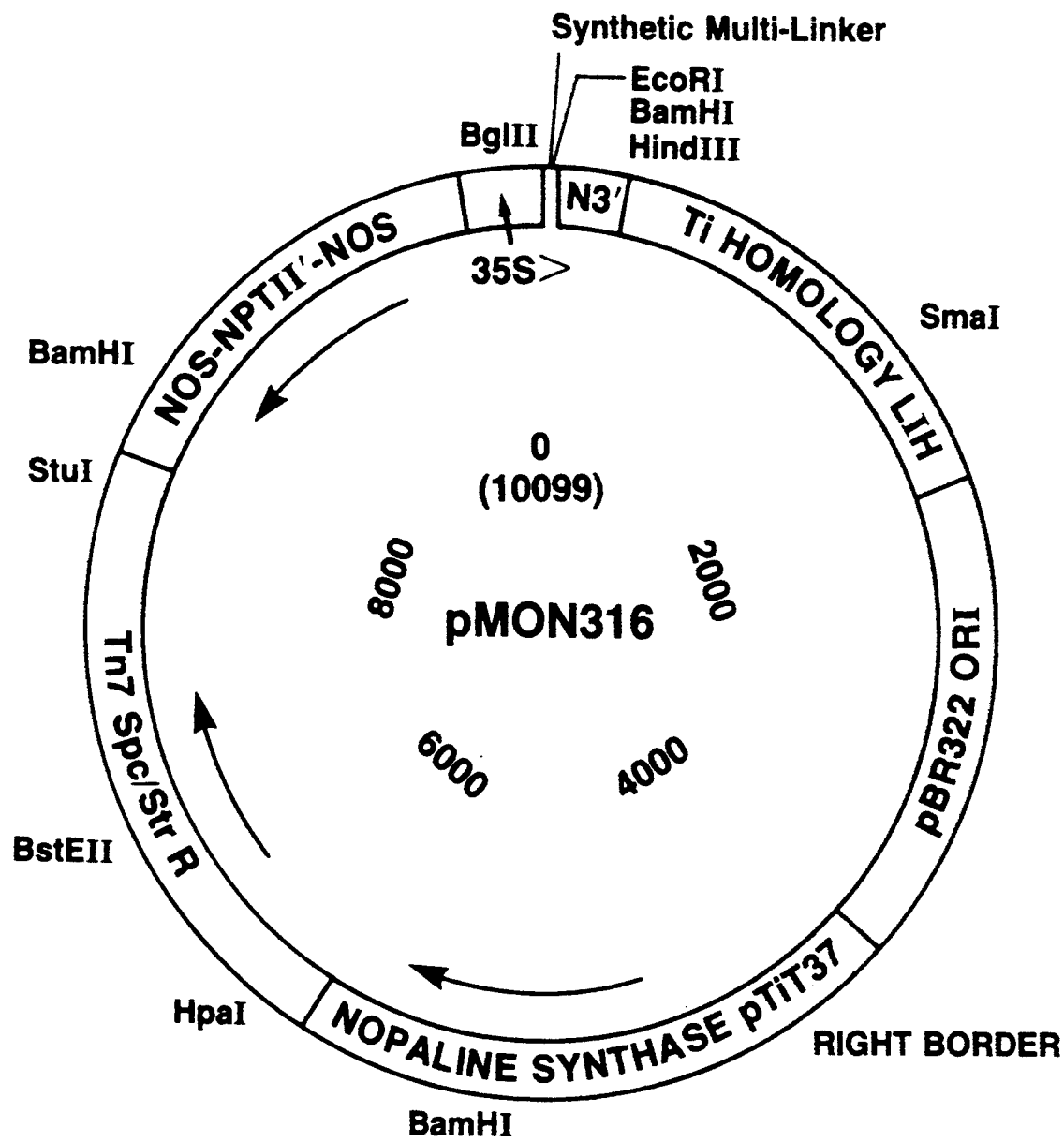
FIG. 5 illustrates plasmid pMON316.

Referring to FIG. 5, plasmid pMON316, a derivative of pMON200 (Fraley, et al., (1985) *Bio/Technology* 3,629–635, Rogers, et al., (1985) *Biotechnology in Plant Sciences*, Academic Press, Orlando, 214–226) is a co-integrating type intermediate vector which contains the CaMV35S promoter and the 3' polyadenylation signal of the NOS gene. pMON316 has unique cleavage sites for the restriction endonucleases BglII, ClaI, KpnI, XhoI and EcoRI located between the 5' leader and the 3' NOS polyadenylation signals. The cleavage sites provide for the insertion of coding sequences carrying their own translational initiation signals immediately adjacent to the CaMV35S leader sequence. Plasmid pMON316 retains all the properties of pMON200 including spectinomycin resistance for selection in *E. coli* and *A. tumefaciens* as well as a chimeric kanamycin gene (NOS/NPTII/NOS) for selection of transformed plant tissue and the nopaline synthase gene for ready scoring of transformants and inheritance in progeny.

Figure 6:
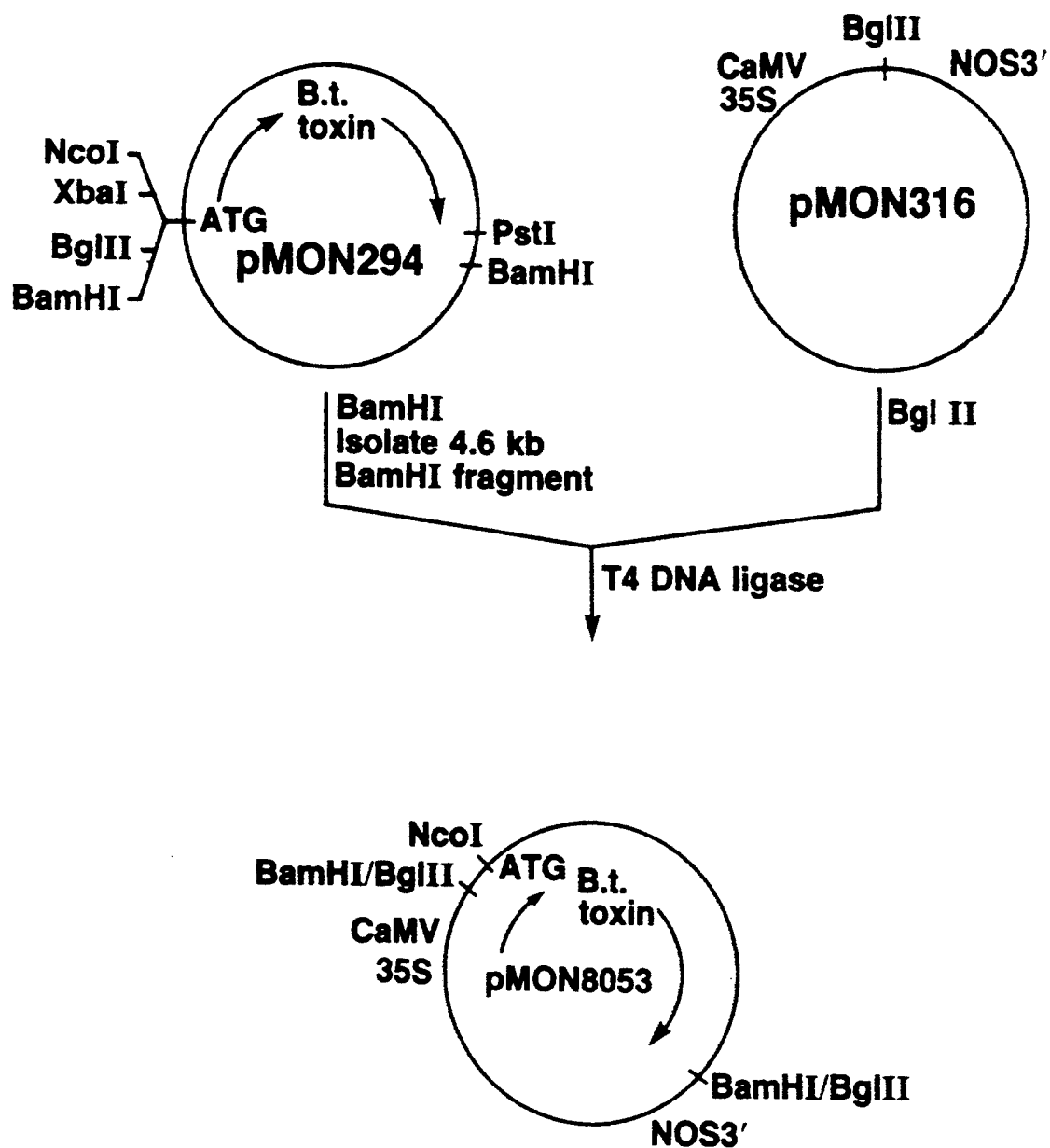
FIG. 6 illustrates the preparation of plasmid pMON8053.

Referring to FIG. 6, a plasmid is constructed for the expression of the *B.t.* toxin gene in plants by ligating the 4.5 kb BamHI fragment containing the toxin gene from pMON294 into pMON316 which had been digested with BglII. A plasmid which contains the toxin gene oriented such that the translational initiation is adjacent to the CaMV35S promoter is identified by digestion with EcoRI and designated pMON8053. Another chimeric plant gene is prepared comprising the full-length construct in which the structural coding sequence for the *B.t.* toxin is truncated at the DraI site at position 3479. This site is 10 nucleotides beyond the translational terminator codon for the coding sequence for the full-length *B.t.* toxin. Thus, this construct contains the full-length coding sequence but very little 3' flanking sequence from the *B.t.* subspecies *kurstaki* gene. This construct is designated pMON9712.

Figure 7:
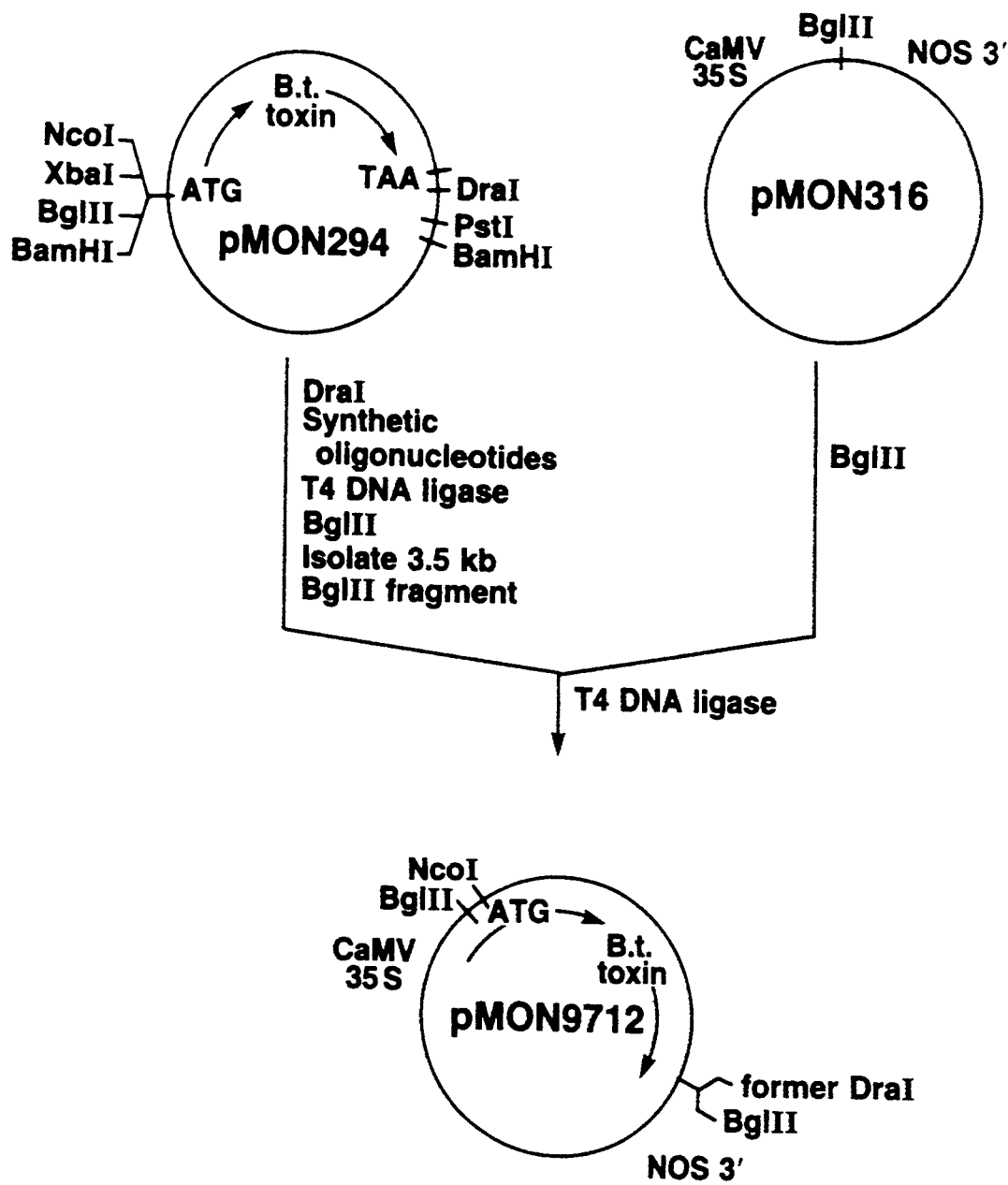
FIG. 7 illustrates the preparation of plasmid pMON9712.

Referring to FIG. 7, plasmid pMON9712 is prepared by digesting pMON294 with endonuclease DraI. A pair of complementary oligonucleotides having the following sequence are synthesized:

5'-TAGTAGGTAGCTAGCCA-3'
3-ATCATCCATCGATCGGTCTAG-5'

When annealed to one another these oligonucleotides encode translational terminators in all three reading frames. The annealed oligonucleotide pair is flush-ended at one end and provides a four nucleotide single-stranded region capable of ligation to BglII digested DNA at the other end. The oligonucleotides are annealed to one another and ligated to pMON294 DNA which had been digested with DraI. The ligated DNA is digested with BglII, and a BglII fragment of approximately 3.5 kb containing the full-length *B.t.* toxin coding sequence is isolated. This fragment extends from the BglII site just upstream of the translational initiation codon to the BglII site created by the oligonucleotide pair. This BglII fragment is ligated with BglII digested pMON316. By digest with EcoRI a clone (pMON9712) is identified in which the translational initiator for the full-length toxin gene is adjacent to the CaMV35S promoter.

EXAMPLE 3

B. Truncated Toxin

Previous work has shown that a fragment of the *B.t.* toxin coding sequence which extends from upstream of the translational initiator to the KpnI site at position 2170 produced a protein which is toxic to *M. sexta* when expressed in *E. coli*. A plant expression vector incorporating such a truncated *B.t.* toxin encoding gene is constructed as follows. Based on the DNA sequence of the toxin gene at the KpnI site at position 2170, a pair of complementary oligonucleotides are synthesized as shown below which when annealed to one another and ligated to the toxin gene at the KpnI site encode two translational termination codons in frame with the toxin coding sequence.

5'-CTAGTAAA-3'
3'-CATGGATCATTTCTAG-5'

Figure 8:
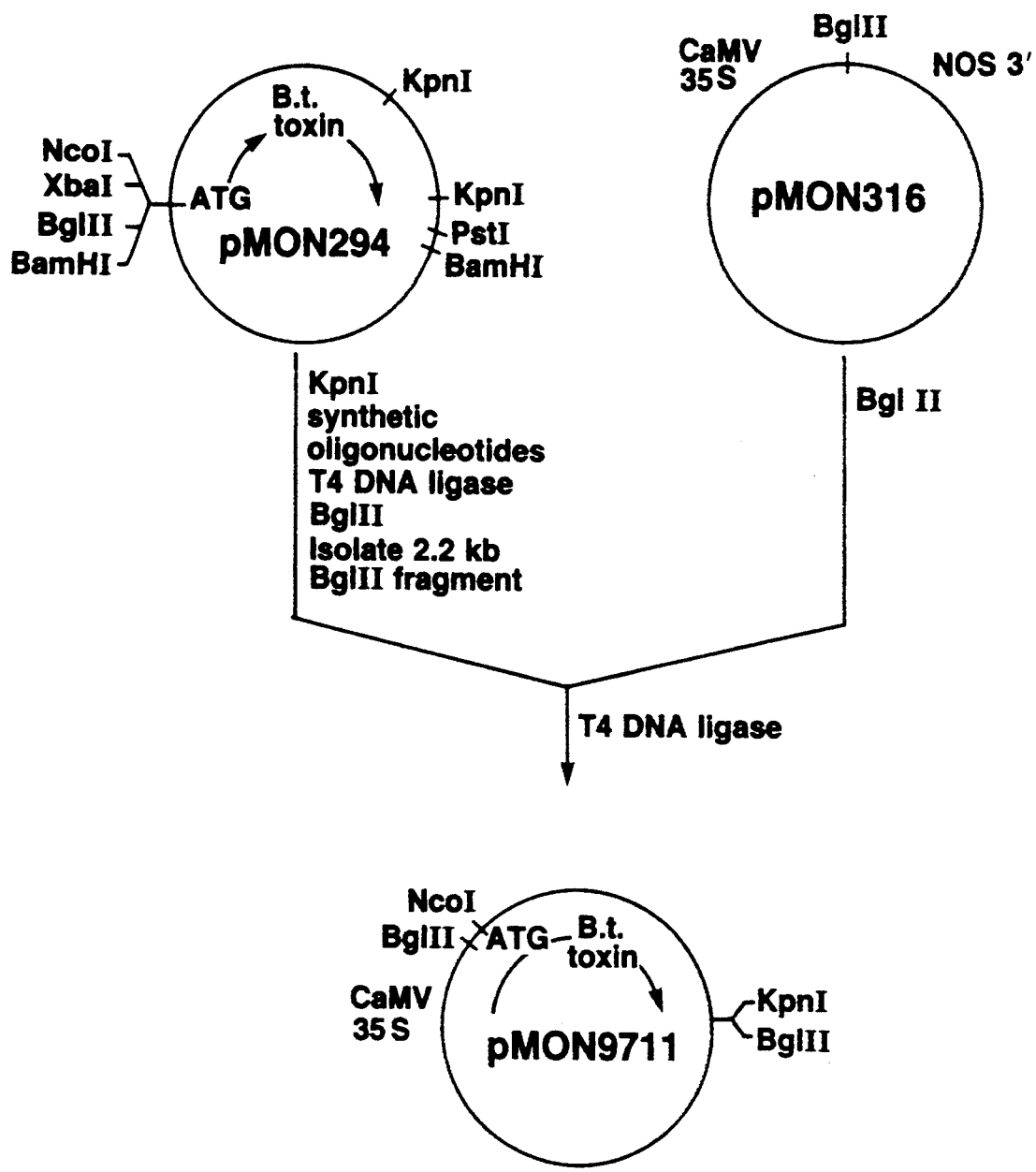
FIG. 8 illustrates the preparation of plasmid pMON9711.

The annealed oligonucleotides provide, at one end, a four nucleotide single-stranded region capable of ligation to KpnI digested toxin gene, and, at the other end, a four nucleotide single-stranded region capable of ligation with BglII digested DNA. Referring to FIG. 8, the oligonucleotides are annealed to one another and ligated with pMON294 which had been digested with KpnI. This ligated DNA is then digested with BglII and a 2.2 kb BglII fragment is isolated. This fragment extends from the BglII site just upstream of the translational initiator of the toxin gene to the BglII site created by the oligonucleotide pair.

A plasmid is constructed for the expression in plants of the B.t. toxin gene truncated at the KpnI site by ligating the 2.2 kb BglII fragment with BglII digested pMON316. A clone is identified by digestion with EcoRI in which the translational initiator for the truncated toxin gene is adjacent to the CaMV35S promoter and is designated pMON9711.

EXAMPLES 4 AND 5

CHIMERIC B.t. TOXIN GENES FOR PLANT TRANSFORMATION USING MAS PROMOTER

Two chimeric B.t. toxin genes are constructed in which the mannopine synthase (MAS) promoter from plasmid pTiA6, an octopine-type plasmid from *Agrobacterium tumefaciens* was used in combination with the B.t. toxin genes contained in previously described constructs pMON9711 and pMON9712.

Figure 9A:
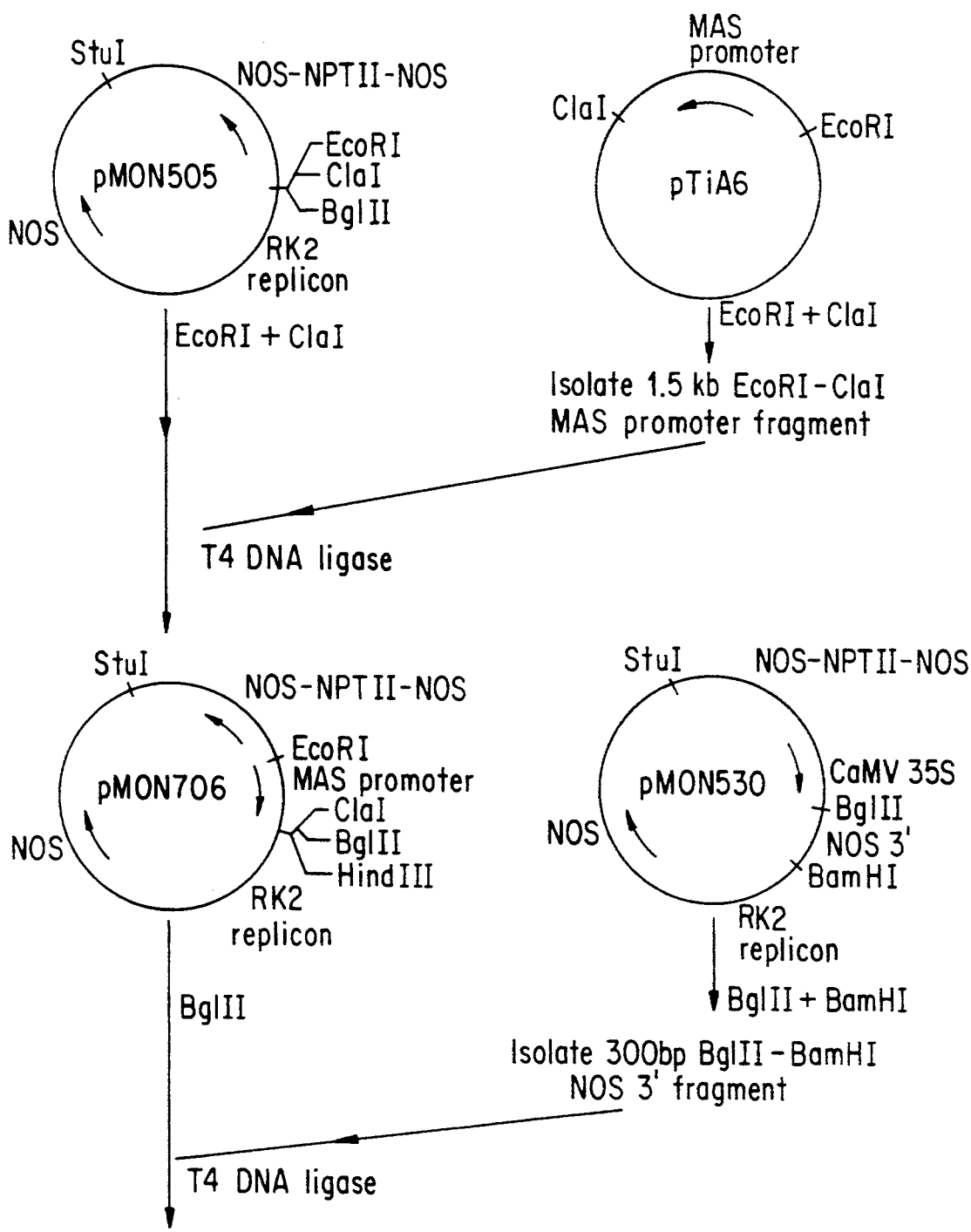
FIGS. 9a–9b illustrates the preparation of plasmid pMON9741.
Figure 9B:
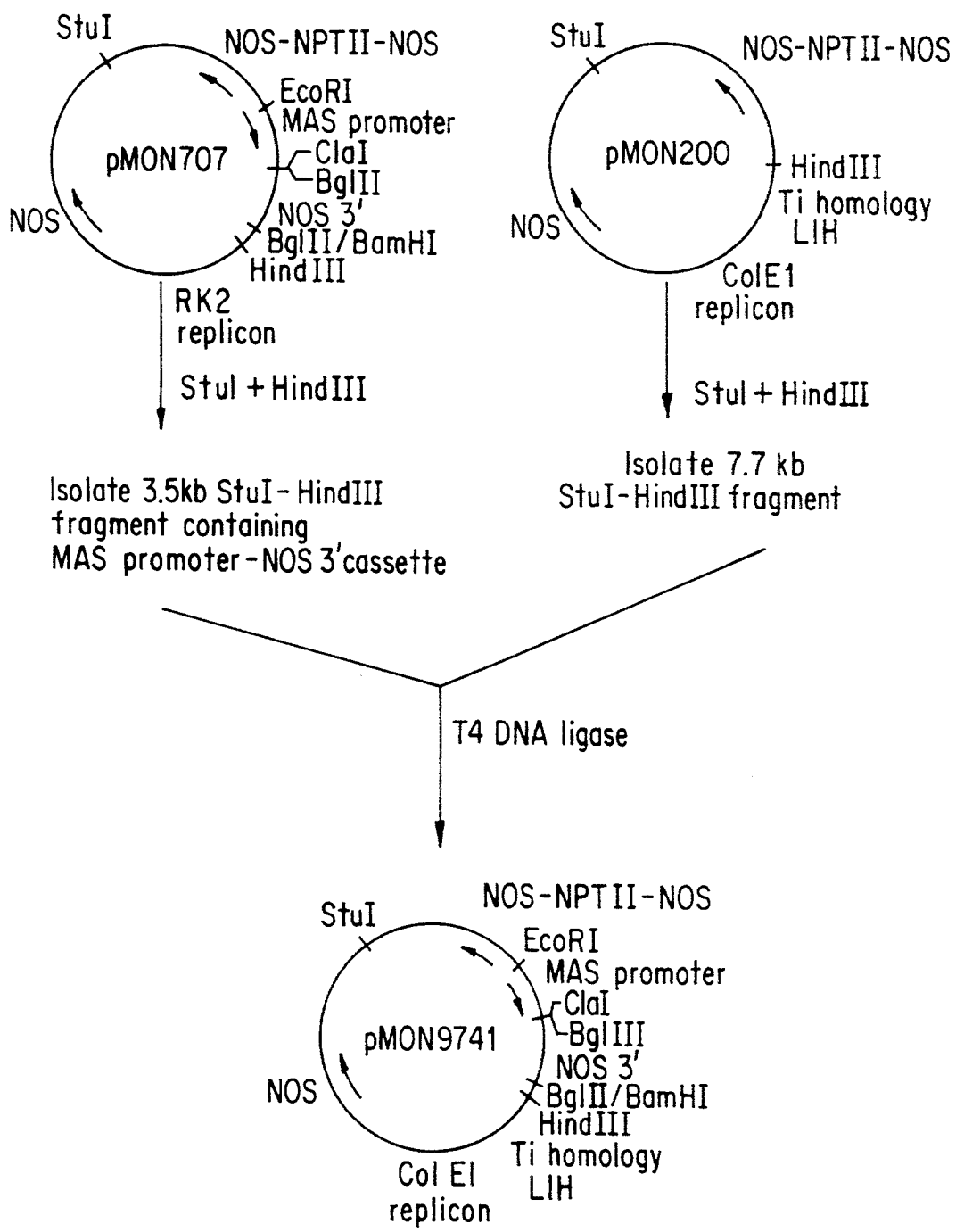

The MAS promoter is isolated from pTiA6 as a 1.5 kb EcoRI-ClaI fragment. This DNA fragment extends from the ClaI site at nucleotide 20,138 to the EcoRI site at 21,631 in the sequence of Barker, et al. (1983) *Plant Mol. Biol.* 2,335-350. Referring to FIG. 9, the EcoRI-ClaI fragment is ligated with the binary vector pMON505, Horsch and Klee (1986) *P.N.A.S.*, USA 83, 4428-4432, which had been previously digested with EcoRI and ClaI. The resulting plasmid is designated pMON706. A fragment containing the NOS 3' end is inserted downstream of the MAS promoter to obtain a MAS-NOS 3' expression cassette vector. The NOS 3' fragment is excised from pMON530 as a 300 bp BglII-BamHI fragment and inserted into BglII-digested pMON706. The resulting plasmid is designated pMON707.

Plasmid pMON530 is constructed by cleavage of pMON200 with NdeI to remove a 900 bp NdeI fragment to create pMON503. Plasmid pMON503 is cleaved with HindIII and SmaI and mixed with plasmid pTJS75, Schmidhauser and Helinski (1985) *J. Bacterial* 164, 155, that had also been cleaved with HindIII and SmaI. A plasmid that contained the 3.8 kb HindIII-SmaI fragment of pTJS75 joined to the 7.8 kb HindIII-SmaI fragment of pMON503 is isolated and designated pMON505. Next the CaMV35S-NOS3' cassette is transferred to pMON505 by cleavage of pMON316 with StuI and HindII and isolation of the 2.5 kb StuI-HindIII fragment containing the NOS-NPTII'-NOS marker and the CaMV35S-NOS3' cassette. This is added to pMON505 DNA cleaved with StuI and HindIII. Following ligation and transformation a plasmid carrying the CaMV35S-NOS3' cassette in pMON505 is isolated and designated pMON530.

Figure 10:
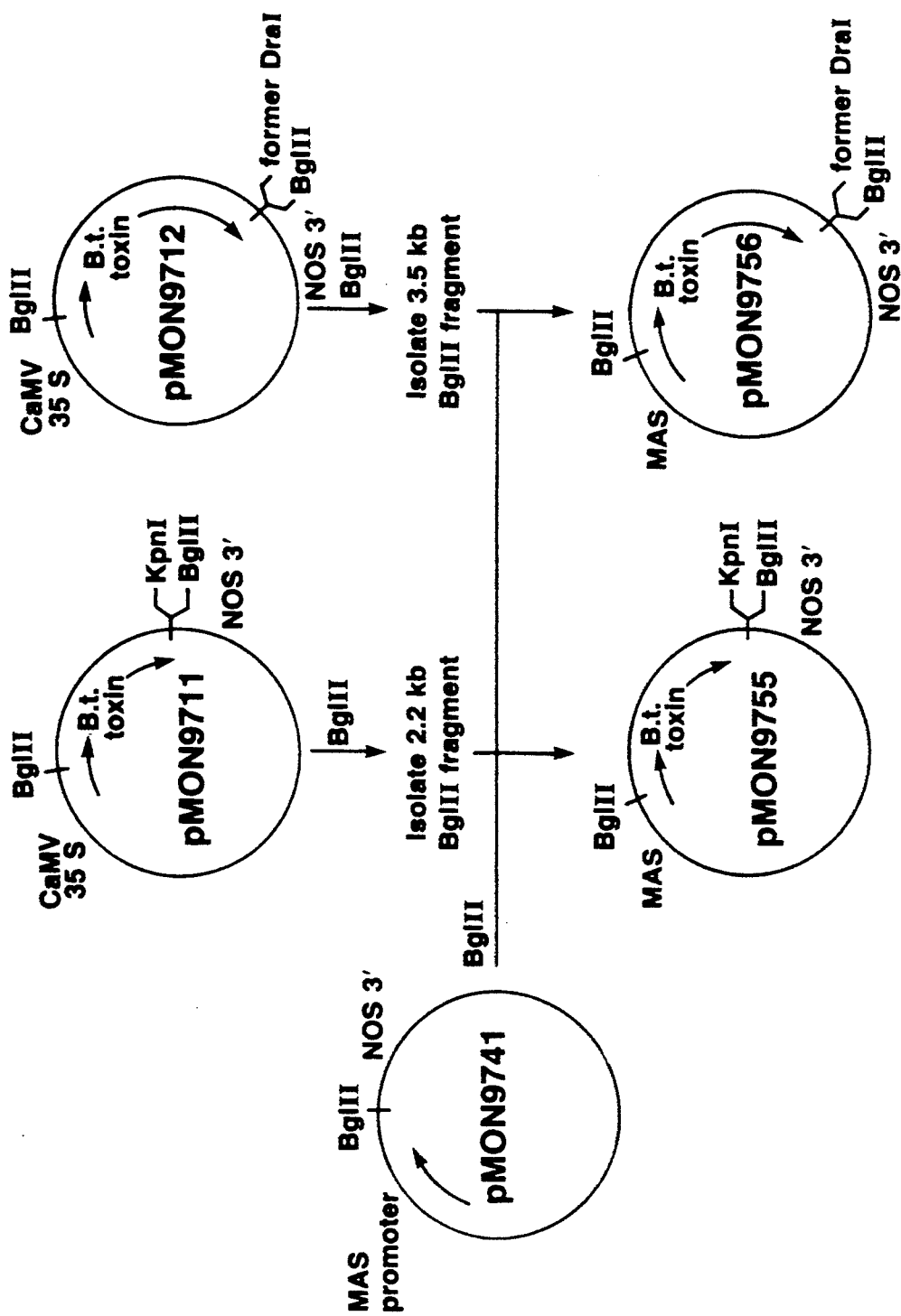
FIG. 10 illustrates the preparation of plasmids pMON9755 and pMON9756.

Since some binary vectors have greatly reduced frequencies of transformation as compared to co-integrating vectors, the MAS-NOS 3' cassette is moved from pMON707 into the co-integrating vector pMON200. Plasmid pMON200 is digested with StuI and HindIII and a 7.7 kb fragment isolated by agarose gel electrophoresis. Plasmid pMON707 is similarly digested with StuI and HindIII and a 3.5 kb StuI-HindIII fragment containing the MAS-NOS 3' cassette is isolated by agarose gel electrophoresis and recovery on a DEAE membrane with subsequent elution with 1M NaCl. These two DNA fragments are ligated and the resulting plasmid is designated pMON9741. This plasmid contains the MAS-NOS 3' cassette in the pMON200 co-integrating background. Chimeric B.t. toxin genes driven by the MAS promoter are prepared. Referring to FIG. 10, the B.t. toxin gene inserts are excised as BglII fragments from pMON9711 and pMON9712. Each of these fragments are ligated with BglII-digested pMON9741. In each case by digestion with EcoRI a clone is obtained in which the 5' end of the B.t. toxin gene is adjacent to the MAS promoter. These plasmids are designated pMON9755 and pMON9756 and contain the B.t. toxin coding sequences from pMON9711 and pMON9712, respectively.

EXAMPLE 6

EXPRESSION OF CHIMERIC B.t. GENES IN LETTUCE PLANTS

Introduction of Intermediate Vectors into Agrobacterium

Intermediate vectors containing pMON200, pMON9711 and pMON9712 are introduced into *Agrobacterium tumefaciens* strains GV3111SE and ASE which contain the disarmed Ti plasmid pTiB6SE described by Fraley, et al. (1985) supra. *Agrobacterium tumefaciens* strains containing co-integrates between pTiB6SE and these intermediate vectors are selected as described below.

Transformation and Regeneration of Lettuce

Transformation and regeneration of transformed lettuce utilizing the *Agrobacterium tumefaciens* strains described above are performed as described by Michelmore, et al. (1987) *Plant Cell Rep.* 6, 439-442.

Seeds of Lettuce (*Lactuca sativa*) cultivar Cobham Green are surface sterilized by dipping them in 75% ethanol for 15 seconds followed by 60 minutes in 10% NaOCl with a trace of Tween-20 detergent followed by two washes in sterile distilled water. The seeds are then placed (25 to 30 seeds/plate) onto 1% agar containing half strength Hoaglands solution and 10 $\mu$g/ml gibberellin acid 3. Seeds are incubated at 27° C. with a 14 hour photoperiod at 800 lux. After four days the cotyledons are cut into four pieces and used for transformation.

Agrobacterium strains 3111SE and ASE containing the B.t. vectors pMON9711 and pMON9712 are grown in Luria broth containing chloramphenicol (25 $\mu$g/ml), kanamycin (50 $\mu$g/ml) and spectinomycin (100 $\mu$g/ml) to a density of approximately $5 \times 10^8$ bacteria/ml. The cut cotyledons are soaked in the bacterial solution for 10 minutes and then placed on filter papers over tobacco cell nurse cultures for 2 days. The nurse culture plates are prepared as follows. Two days prior to cocultivation, 3 ml of a log phase cell suspension of *Nicotiana plumbaginifolia* is pipetted onto plates containing RMNO tobacco nutrient medium (3 mg/l indole acetic acid, 0.06 mg/l kinetin) and incubated as described above for lettuce seed. Filter papers (Whatman #2, 9 cm) are soaked in liquid RMNO medium and autoclaved. A filter paper is laid over the nurse culture just prior to placing the lettuce cotyledons on the filters.

All incubations of the lettuce explants are performed under the conditions described above. The lettuce explants are incubated over the nurse cultures for 2 days with no kanamycin or carbenicillin in the medium. The explants are then transferred and incubated for 12 days on callus initiation medium (Shenk and Hildebrandt nutrient medium plus 0.1 mg/l indole acetic acid and 0.05 mg/l kinetin) containing 50 mg/l kanamycin and 500 mg/l carbenicillin. The callus that formed are subcultured every 2 weeks on regeneration medium (Shenk and Hildebrandt nutrient medium plus 0.05 mg/l kinetin and 0.05 mg/l zeatin) containing 50 mg/l kanamycin and 500 mg/l carbenicillin. Confluent callus formed around all explants. Approximately 10% of the explants formed shoots from 3 weeks onward.

Shoots developed on the regeneration medium to about but no longer than 5 mm are excised from the callus, dipped in 10 mg/l indole acetic acid, placed on rooting medium (Shenk and Hildebrandt nutrient medium) containing 50 mg/l kanamycin and incubated as described above. After 2 to 5 weeks, roots began to develop. After roots have developed, plantlets are transferred to vermiculite and incubated in a growth room at 15° C. to prevent bolting. When the plantlets are about 6 cm high, they are transplanted into soil mix and grown to maturity in a greenhouse.

When the plantlets are transferred to vermiculite, leaf explants are taken and plated on callusing medium with 50 mg/l kanamycin to confirm transformation. Opine production is also analyzed in sap from these plantlets to confirm transformation.

Insect Feeding Assays of Transformed Lettuce Plants

Toxicity of transformed lettuce plants containing chimeric B.t. toxin genes are determined by feeding assays with test insects. Leaves are removed from transgenic lettuce plants and placed in sterile 82 mm Petri dishes containing moistened sterile filter paper. Ten to twenty insect larvae are applied to the leaves and allowed to feed for four days at which time the larvae are scored for mortality and relative growth. All assays are performed at room temperature.

$R_0$ plants (primary transformants) are grown and seed harvested. $R_1$ plants are grown from the seed of the $R_0$ plants. Nopaline positive $R_1$ plants are assayed for insect toxicity. Assays are performed with newly hatched larvae of Heliothis virescens (tobacco budworm). Three different assays are performed at different times. The first three digits of the plant number identifies the parent primary transformants and the last digit identifies different $R_1$ progeny. In the first assay, the control is an $R_1$ progeny of a plant transformed with a vector imparting antibiotic resistance but containing no B.t. gene. No control is used in the second assay. In the third assay, untransformed plants are used as controls. The data is summarized in Table 1.

TABLE 1

| PLANT NUMBER | VECTOR | #LARVAE DEAD/#LARVAE TESTED | | |
|---|---|---|---|---|
| | | Assay 1 | Assay 2 | Assay 3 |
| Nontransformed Controls | None | — | — | 4/10 |
| | None | — | — | 3/10 |
| | None | — | — | 2/10 |
| 228-1 | 200 | 1/10 | — | — |
| 233-5 | 9712 | 7/10s | 19/20 | — |
| 233-6 | | 7/10s | 12/20 | — |

TABLE 1-continued

| PLANT NUMBER | VECTOR | #LARVAE DEAD/#LARVAE TESTED | | |
|---|---|---|---|---|
| | | Assay 1 | Assay 2 | Assay 3 |
| 233-8 | | 9/10s | 12/20 | — |
| 233-9 | | 5/10 | 18/20 | — |
| 233-10 | | 6/10 | 13/20 | — |
| 233-12 | | 6/10 | 14/20 | — |
| 237-1 | 9712 | 3/10 | 10/20 | — |
| 237-2 | | 4/10 | 9/20 | — |
| 237-3 | | 7/10s | 20/20 | — |
| 237-4 | | — | — | 9/10 |
| 237-5 | | — | — | 7/10 |
| 237-6 | | — | — | 10/10 |
| 237-7 | | — | — | 9/10 |
| 238-11 | 9711 | 1/10 | — | — |
| 238-13 | | 3/10 | — | — |
| 238-17 | | 7/10s | 16/20 | — |
| 305-1 | 9711 | — | — | 7/10 |
| 305-2 | | — | — | 4/10 |
| 305-3 | | — | — | 2/10 |
| 308-1 | 9711 | — | — | 7/10 |
| 308-2 | | — | — | 6/10 |
| 308-4 | | — | — | 7/10 |
| 308-7 | | — | — | 10/10 |

"s" indicates that surviving larval are stunted

The data show that lettuce plants containing the B.t. gene are toxic to H. virescens at levels significantly above the controls. In addition, the data further show that toxicity is inherited because all plants tested are progeny, not primary transformants. The $R_1$ plants tested are a mixture of heterozygotes and homozygotes which could account for some of the variation in activity since homozygotes containing two copies of the B.t. gene would be more active plants.

Although the invention has been illustrated by typical examples, it is not limited thereto. Changes and modifications of the examples of the invention herein chosen for purposes of disclosures can be made which do not constitute departure from the spirit and scope of the invention.

The embodiments of the invention in which an exclusive property or privilege is claimed are defined as follows:

We claim:

1. A plant of the genus Lactuca which has been regenerated from a plant cell transformed to comprise a full length Bacillus thuringiensis crystal protein gene capable of encoding a Bacillus thuringiensis crystal protein of approximately 130–135 kD under control of a promoter such that said gene is expressible in said plant in amounts insecticidal to Lepidopteran insects.

2. A plant cell of genus Lactuca transformed to comprise a full length Bacillus thuringiensis crystal protein gene capable of encoding a Bacillus thuringiensis crystal protein of approximately 130–135 kD under control of a promoter such that said gene is expressible in said plant cell in amounts insecticidal to Lepidopteran insects.

3. The plant of claim 1 in which the plant is Lactuca sativa.

4. The plant of claim 1 in which the coding sequence encodes the protein encoded by the DNA sequence 1-3471 of FIG. 1.

5. The plant of claim 1 which exhibits toxicity toward Heliothis virescens.

6. The plant of claim 4 which exhibits toxicity toward Heliothis virescens.

7. The cell of claim 2 in which the plant cell is Lactuca sativa.

8. The cell of claim 2 in which the coding sequence encodes the protein encoded by the DNA sequence 1-3471 of FIG. 1.

9. The cell of claim 2 which exhibits toxicity toward Heliothis virescens.

10. The cell of claim 8 which exhibits toxicity toward Lepidopteran of the genus Heliothis virescens.

* * * * *